(12) United States Patent
Mendoza et al.

(10) Patent No.: US 6,535,658 B1
(45) Date of Patent: Mar. 18, 2003

(54) HYDROGEN SENSOR APPARATUS AND METHOD OF FABRICATION

(75) Inventors: Edgar A. Mendoza, Redondo Beach, CA (US); Anil Menon, Torrance, CA (US)

(73) Assignee: Optech Ventures, LLC, Torrance, CA (US)

(*) Notice: Subject to any disclaimer, the term of this patent is extended or adjusted under 35 U.S.C. 154(b) by 24 days.

(21) Appl. No.: 09/639,007

(22) Filed: Aug. 15, 2000

(51) Int. Cl.[7] .................... G02B 6/00; G01N 33/18; G01J 1/04

(52) U.S. Cl. .................... 385/12; 385/31; 385/38; 73/23.2; 250/227.11; 250/227.14; 250/573

(58) Field of Search ................ 385/12, 31, 24, 385/14, 38, 79; 250/227.11, 227.14, 227.23, 227.18, 227.19, 573; 65/385; 73/23.2, 24.02; 356/445

(56) References Cited

U.S. PATENT DOCUMENTS

| | | | | |
|---|---|---|---|---|
| 4,872,759 A | * | 10/1989 | Stich-Baumeister et al. | 356/432 |
| 5,107,316 A | * | 4/1992 | Jelley et al. | 357/25 |
| 5,290,103 A | * | 3/1994 | Fevrier et al. | 374/131 |
| 5,708,735 A | * | 1/1998 | Benson et al. | 385/12 |
| 5,835,229 A | * | 11/1998 | Daniels | 356/435 |
| 6,006,582 A | * | 12/1999 | Bhandari et al. | 73/23.2 |

* cited by examiner

*Primary Examiner*—Brian Healy
(74) *Attorney, Agent, or Firm*—Lawrence S. Cohen

(57) ABSTRACT

A porous glass rod is treated to include tungsten oxide and palladium in an arrangement that is sensitive to hydrogen to produce a color change that is a function of the hydrogen concentration. The rod is attached to the tip of a double fiber into one of which light is launched by a light source. A detector at the end of the second fiber is responsive to light reflected by the rod. The process for forming the rod includes the steps of doping the glass with a tungsten compound and a palladium compound with intervening and subsequent heating steps to bond the tungsten oxide and palladium to available oxygen atoms of the porous glass.

24 Claims, 4 Drawing Sheets

HYDROGEN SENSOR APPARATUS AND METHOD OF FABRICATION

BACKGROUND OF THE INVENTION

This invention relates to hydrogen sensors and more particularly to such sensors that produce a color change in the presence of hydrogen.

Fiber optic hydrogen sensors are available commercially. Such apparatus employ an optical fiber with a thin palladium or platinum film at the tip of the fiber. The thickness of the film changes in the presence of hydrogen. A light source directs light down the length of the fiber and a detector senses an interference pattern representative of the distance between the fiber tip and the surface of the film (i.e. the film thickness); a function of the presence of hydrogen. This type of apparatus is sensitive to the presence of from zero to one percent of hydrogen.

In another type of commercially available fiber optic hydrogen sensor, an optical fiber includes a Bragg grating with a palladium film deposited over the grating. The fiber is stretched and in the presence of hydrogen, the palladium film affects the characteristics of the fiber to alter the wavelength of light reflected by the grating. In use, a light source, launching light down the fiber, produces a reflected wave at a wavelength representative of the presence of hydrogen. The greater the hydrogen concentration, the greater the change in the grating wavelength. This apparatus is sensitive to the presence of hydrogen from zero to ten percent concentration.

In a third known apparatus, a film of palladium is formed at the end of a fiber with a tungsten oxide coating formed over the palladium. In the presence of hydrogen, the palladium film places a charge on the tungsten oxide that changes its color.

Each of these commercially available apparatus is typically fabricated with an external thin metal film at the termination of the fiber that is susceptible to contamination, scratching, and other environmental factors. As a result, the sensors are limited in sensitivity, relatively expensive to manufacture, have a limited lifetime, and can produce unreliable results.

BRIEF SUMMARY OF THE INVENTION

In accordance with the principles of this invention, one embodiment of the sensor comprises a hydrogen sensing element of porous silica glass, having a matrix of tungsten oxide and palladium in energy coupled proximity, fabricated in the form of a tiny rod, typically of cylindrical geometry, with a diameter of three millimeters and a length of five millimeters. The sensor can also be fabricated in other forms including, but not limited to, rectangular, square, and disk formats. The porous glass rod is doped with a solution of a photosensitive tungsten hexacarbonyl ($W(CO)_6$) compound in an alcohol solvent to entrap the compound in the glass. The rod is next exposed to ultraviolet light, to induce a photochemical reaction transforming the tungsten hexacarbonyl compound into tungsten oxide ($WO_3$) and permanently binding the tungsten oxide to oxygen atoms in the silica glass. A heating process drives off the solvent and removes the photoproduced CO gas, leaving tungsten oxide permanently bound to the silica matrix of the porous glass. The rod is then doped with a palladium tetrachloride ($PdCl_4$) solution, and heated to break the $PdCl_4$ molecules into palladium metal and chlorine gas and to evaporate the chlorine gas from the porous glass matrix, leaving palladium metal deposited on the glass surface.

When hydrogen is present, the $Pd/WO_3$ complex causes a partial redox reaction of the tungsten oxide and palladium metal to produce a color change in the glass rod representative of the hydrogen concentration. The rod may further include a coating to reduce the sensor's sensitivity to moisture and other environmental contaminants.

The unique chemochromatic process of the invention binds tungsten oxide and palladium into the porous glass volume of the sensing element, thereby eliminating the need for external surface films. As such, the sensing chemistry is embedded in a relatively large, three-dimensional, pore volume, compared to that of a two-dimensional surface film, providing improved sensor sensitivity and increased immunity to contaminants that may be present on the surface of the sensing tip. In addition, the use of a wet chemistry process, instead of a thin film fabrication process, reduces manufacturing costs and produces a more rugged and reliable sensor structure.

In an apparatus of the invention, the sensing rod, prepared as above, is attached to the tip of a double fiber arrangement whereby light launched into one fiber is passed through the sensing rod, reflected from the back surface of the rod and launched into the second fiber where it is brought to an optoelectronic detection and signal processing unit. In the presence of hydrogen, the spectrum of transmitted light shifts, producing a color (wavelength) change that is transformed into an intensity change by the optoelectronic detection units. The invention is sensitive to hydrogen concentrations in the range of zero to one hundred percent with maximum sensitivity in the zero to five percent range and with a resolution of 0.1% hydrogen.

In another apparatus of the invention, a multi-point fiber optic sensor system (MFOS) is constructed using multiple sensing elements distributed along a communication bus. An optoelectronic readout system connected to the bus is adapted to display the concentration profiles of individual sensor readouts. The system can be used, for example, to monitor gas leaks in launch vehicle fuel tanks and can be distributed along automobile fuel cells.

In another apparatus of the invention, a sensor package is constructed with a hydrogen sensitive element and a temperature sensitive element in close proximity so that the signal returned from the hydrogen element can be compensated for temperature fluctuations.

In another embodiment, the sensing element can be in the form of a porous glass film or layer treated as the herein described matrix of tungsten oxide and palladium in energy coupled proximity for hydrogen sensing and which can be applied to a supporting substrate.

DETAILED DESCRIPTION OF THE INVENTION

Figure 1:
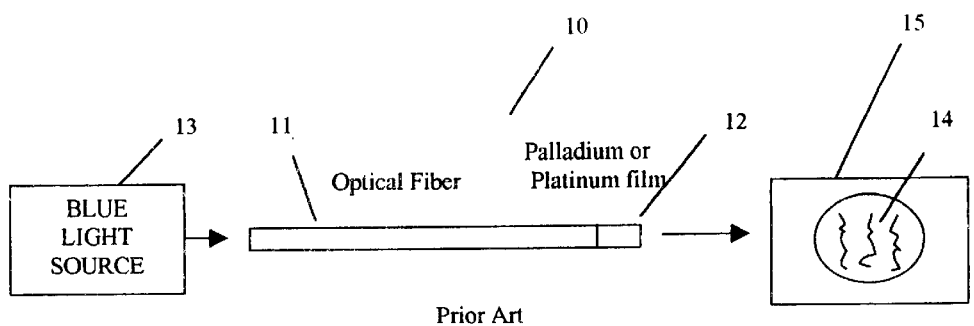
FIGS. 1, 2, and 3 are schematic representations of prior art hydrogen sensor apparatus.

Referring to FIG. 1, one type of commercial hydrogen sensor apparatus 10 comprises a blue light source 13, an optical fiber 11 having a thin film palladium or platinum tip 12, and a detector 15. In use, the source 13 directs light down the fiber 11 to the tip 12 causing a reflected light interference pattern that is measured by the detector 15. The fringe pattern in the interference signal gives a direct indication of the thickness of the palladium film. In the presence of hydrogen, the thickness of the tip 12 changes producing an interference pattern 14 in the detector 15, representative of the presence of hydrogen.

Figure 2:
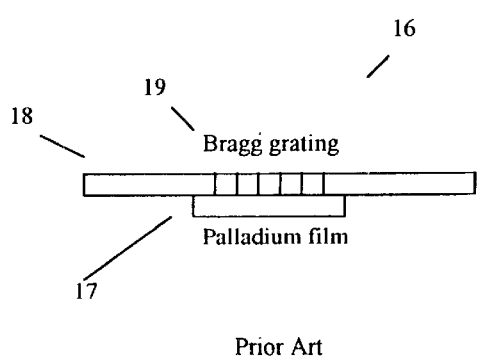

Referring to FIG. 2, another type of commercial hydrogen sensor 16 detects the presence of hydrogen by using a palladium film 17 deposited over a Bragg grating 19 in an optical fiber 18. The fiber 18 is stretched and the deposited film 17 covers the grating 19. In use, light launched down the fiber 18 is reflected by the Bragg grating 19 at a specific wavelength, determined by the grating geometry. In the presence of hydrogen, the film 17 alters the grating characteristics to produce reflected light at a wavelength representative of the hydrogen concentration.

Figure 3:
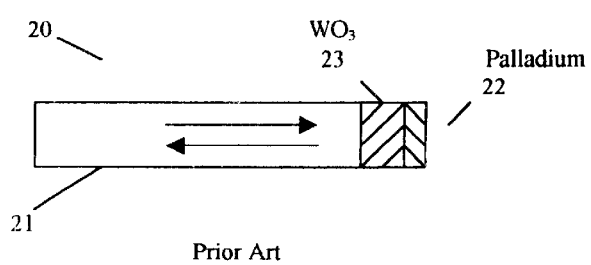

Referring to FIG. 3, another type of commercial hydrogen sensor 20 comprises an optical fiber 21 coated with a tungsten oxide film 23 and a palladium film 22 on top. In use, the palladium tip 22 places a charge on the tungsten oxide 23 when hydrogen is present, causing the tip to change color.

Figure 4:
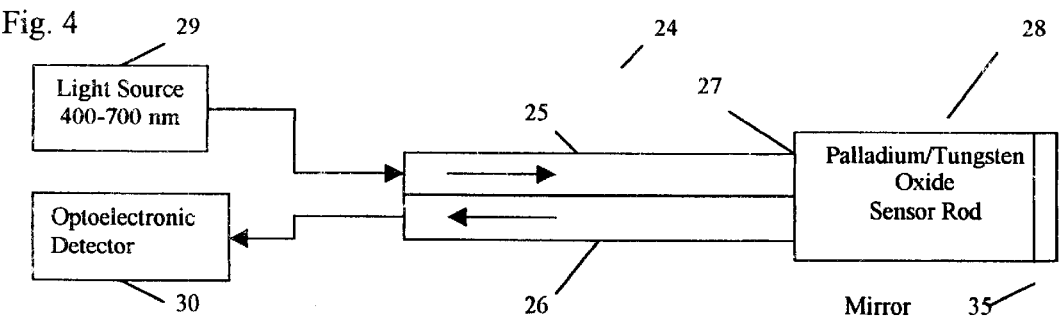
FIG. 4 is a schematic representation of a hydrogen sensor apparatus in accordance with the principles of this invention.

Referring to FIG. 4, a hydrogen sensor apparatus 24 of the invention comprises a transmitting fiber 25 and a reflecting fiber 26 in a dual optical fiber arrangement forming a common tip 27. The tip 27 is fitted with a palladium/tungsten oxide sensor rod 28 fabricated in accordance with the principles of the invention. The rod 28 may include a mirrored surface 35. A light source 29 within the range of 400 to 700 nanometers is coupled to the transmitting fiber 25 and an optoelectronic detection unit 30 is coupled to the reflecting fiber 26. In use, light from the source 29 is launched down the transmitting fiber 25 to the sensor rod 28 where it is reflected by mirrored surface 35 and transmitted through the reflecting fiber 26 to the detection unit 30. In the presence of hydrogen, the sensor rod 28 causes a shift in the wavelength and color of light measured by the detection unit 30 as a function of the hydrogen concentration. The detection unit 30 transforms the wavelength shift to an intensity change representation of the hydrogen concentration.

Figure 5:
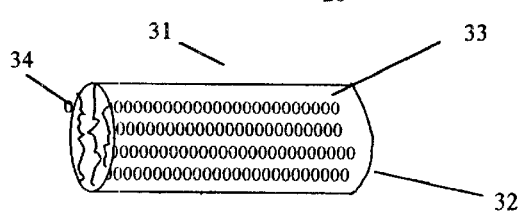
FIG. 5 is a schematic representation of a porous glass rod sensor for use in the apparatus of FIG. 4.

Referring to FIG. 5, the hydrogen sensor 31 of the invention comprises a transparent cylindrically shaped silica glass rod 32 having dimensions of three millimeters in diameter and five millimeters in length. The pores of the glass are in the range of thirty to seventy angstroms. The glass matrix of the sensor rod contains equal concentrations of tungsten oxide 34, bound to oxygen atoms of the glass, and palladium on the surface 33. In use, the palladium causes the tungsten oxide to change color in the presence of hydrogen.

Figure 6:
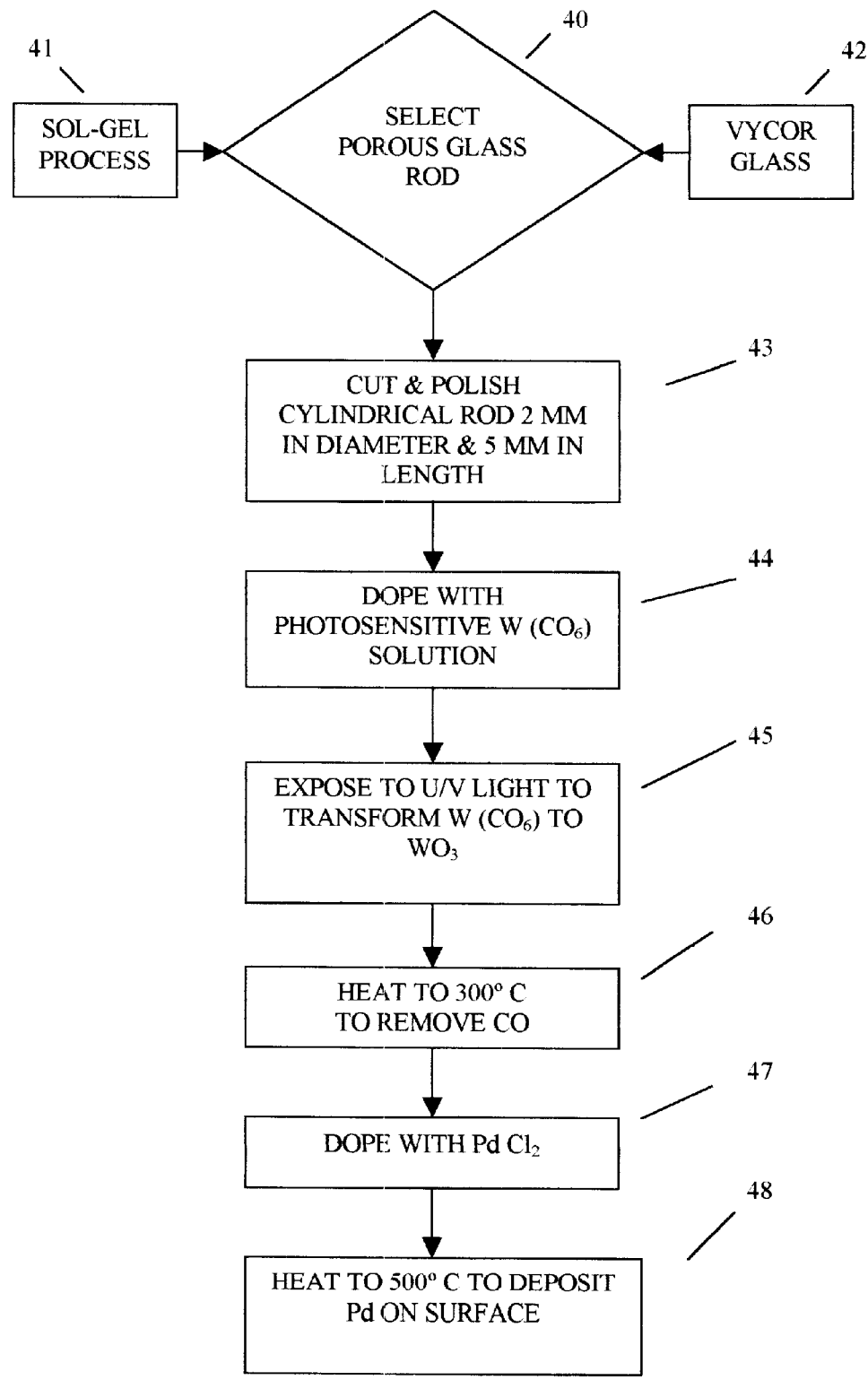
FIG. 6 is a flow diagram of the process for fabricating the sensor of FIG. 5.

Referring to FIG. 6, the process for fabricating the hydrogen sensor comprises the steps of selecting a cylindrical porous glass rod as shown in block 40 by forming a porous silica glass rod using a sol-gel process as illustrated in block 41 or alternatively selecting a commercially available porous Vycor glass rod (PVG) as shown in block 42. The rod is preferably cylindrical in shape and is cut and polished to dimensions of 3 mm in diameter and 5 mm in length, as shown in block 43. The glass is then doped, using a solution process, with photosensitive tungsten hexacarbonyl $W(CO_6)$ as illustrated in block 44.

The $W(CO_6)$ compound, entrapped in the porous matrix of the glass, is next exposed to ultraviolet (UV) light, as indicated in block 45, to transform the $W(CO_6)$ compound to tungsten oxide $(WO_3)$ and permanently bind it to the oxygen atoms of the glass. The glass is then heated to 300° C. to remove the photo-produced CO gas, as shown in block 46. Palladium is then introduced by doping the glass rod with palladium tetrachloride $PdCl_4$, in solution, as shown in block 47 and heating the rod to 500° C., as shown in block 48, to break the chlorine bonds, leaving palladium on the surfaces of the glass pores. This process results in the porous glass having a matrix of tungsten oxide and palladium in energy-coupled proximity that will produce a spectral color change in the presence of hydrogen.

Figure 7:
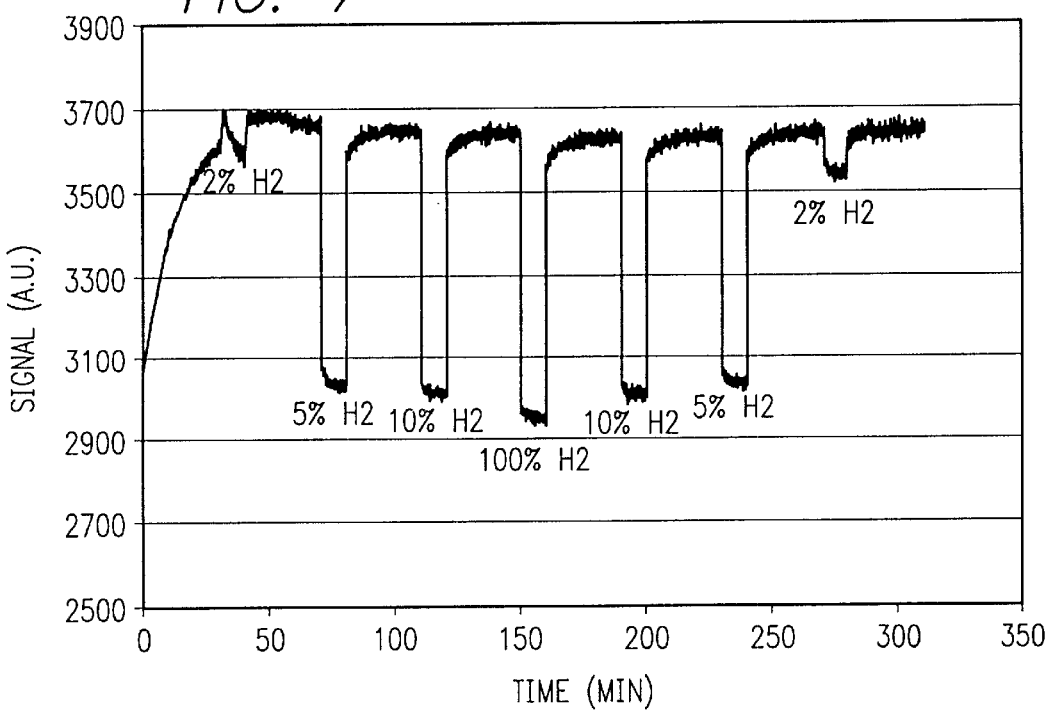
FIG. 7 is a plot of the transmission spectrum versus hydrogen concentration for the sensor of FIG. 5 in the apparatus of FIG. 4.

FIG. 7 shows a plot 50 of the response of the sensor rod of the invention to hydrogen concentrations in the range of 0% to 100%. As indicated, the sensor exhibits maximum sensitivity in the 0% to 5% range.

In another embodiment, the sensing element can be in the form of a porous glass film or layer treated as the herein described matrix of tungsten oxide and palladium in energy coupled proximity for hydrogen sensing and which can be applied to a supporting substrate.

Figure 8:
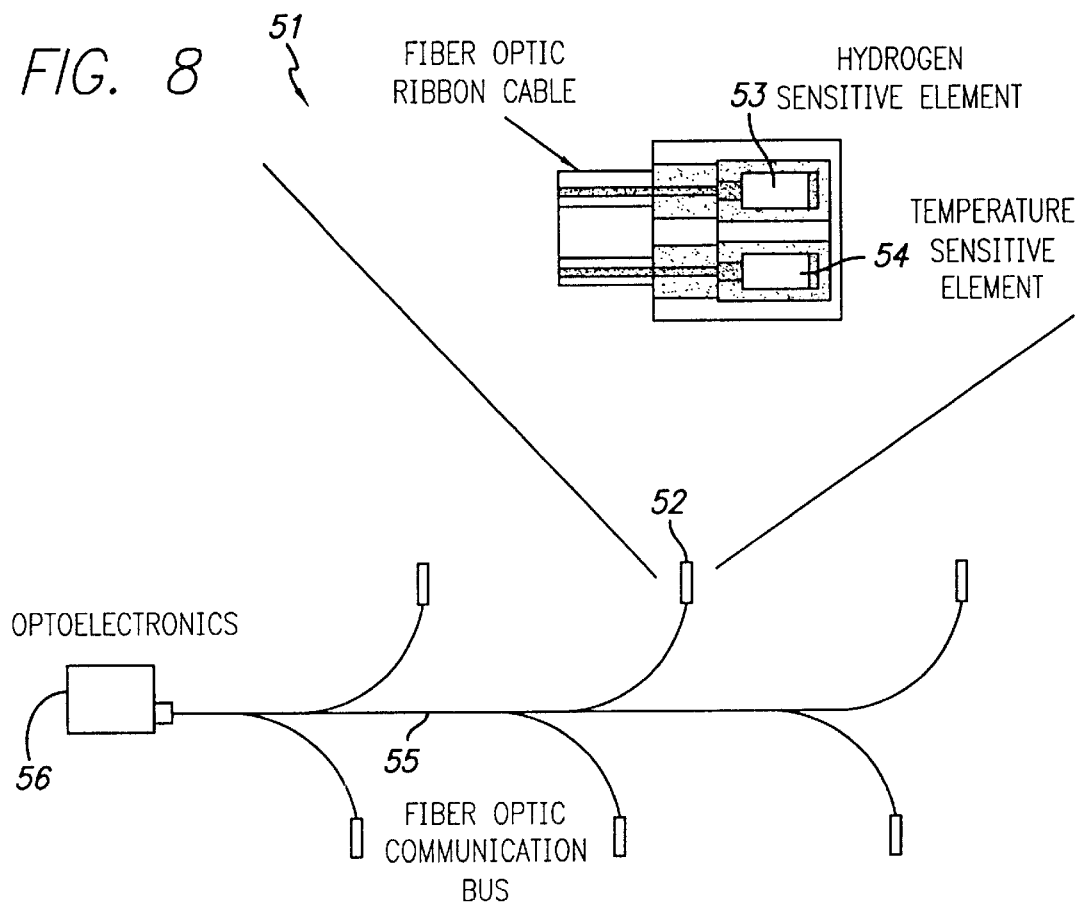
FIG. 8 is a schematic representation of a multi-point fiber optic sensor system and FIG. 9 is a schematic representation of an optoelectronic readout module using an intensity based ratiometric system.

A multi-point fiber optic sensor system 51 using multiple sensors of the invention is shown in FIG. 8. Each sensor 52, containing a hydrogen sensitive element 53 and a temperature sensitive element 54, is connected to a fiber optic communication bus 55. In use, information disseminated along the bus is received by an optoelectronic readout system 56 capable of displaying the hydrogen concentration and temperature profiles of each element.

Figure 9:
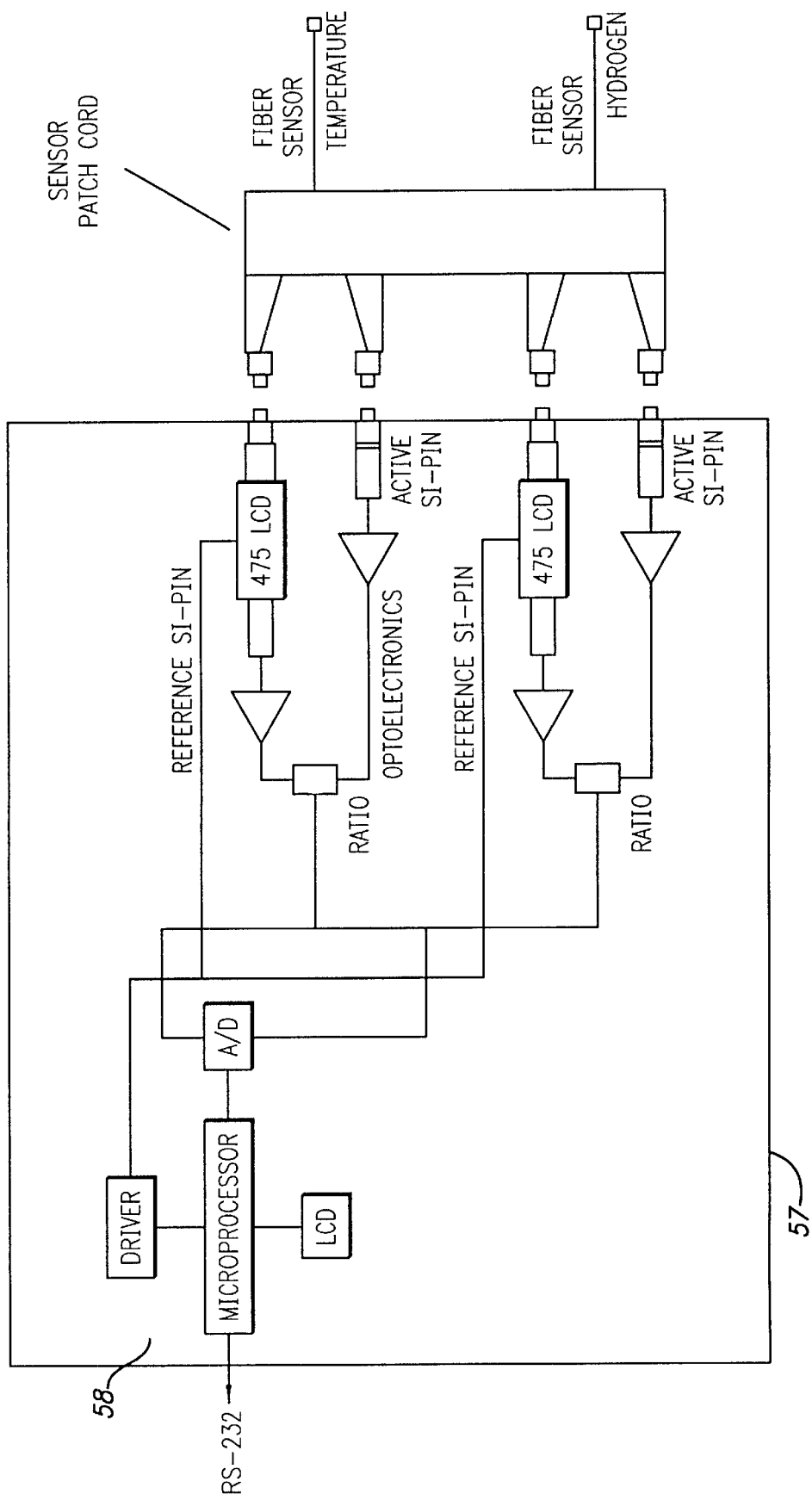

FIG. 9 shows an optoelectronic readout module 57 using an intensity based ratiometric system designed to receive inputs from three sensors. The module circuitry includes a built-in microprocessor 58 to compensate for fluctuations in temperature and light intensity signals.

The unique process of the invention, using photochemical and solution-based techniques to immobilize indicator materials inside a porous structure, can be applied to many other sensor embodiments for specific chemical indicator applications.

Although the various features of novelty that characterize the invention have been described in terms of certain preferred embodiments, other embodiments will become apparent to those of ordinary skill in the art, in view of the disclosure herein. Accordingly, the present invention is not intended to be limited by the recitation of the preferred embodiments, but is instead intended to be defined solely by reference to the appended claims.

What is claimed is:

1. Hydrogen sensor apparatus, said apparatus including first and second optical fibers, each of said fibers having a proximal and a distal end, said fibers forming a common tip at the proximal ends thereof, a porous glass body attached to said common tip, said body including tungsten oxide and palladium in energy-coupled proximity, said apparatus Including a source of light for launching light into the distal end of said first fiber, said apparatus including means coupled to the distal end of said second fiber for detecting the wavelength of light reflected by said porous glass body.

2. The porous glass rod of claim 1 wherein said body is cylindrical in shape with dimensions of about three millimeters in diameter and about five millimeters in length.

3. The porous glass body of claim 1 wherein the glass pores are in the range of thirty to seventy angstroms.

4. A hydrogen sensing element of porous glass said glass having a matrix of tungsten oxide and palladium in energy coupled proximity said element producing a spectral color change in the presence of hydrogen.

5. The hydrogen sensing element of claim 4 wherein the pores of said glass are in the range of thirty to seventy angstroms.

6. The hydrogen sensing element of claim 4 wherein said spectral color change depends directly on the hydrogen concentration.

7. The hydrogen sensing element of claim 4 wherein said spectral color change is in the range of four hundred nanometers to 700 nanometers.

8. The hydrogen sensing element of claim 4 wherein said matrix comprises equal proportions of tungsten oxide and palladium.

9. The hydrogen sensing element of claim 6 wherein said hydrogen concentration is in the range of zero to one hundred percent hydrogen.

10. Hydrogen sensor apparatus comprising a glass rod having proximal and distal ends, said distal end including tungsten oxide and palladium in energy coupled relationship, said tungsten oxide being bound to the glass at said distal end intermingled with palladium atoms.

11. A multi-point gas sensing network comprising;
a multiplicity of fiber optic sensing elements at least one of said sensing elements being a temperature sensing element;
an optoelectronic module containing sensor readout circuitry;
a fiber optic communication bus, said module and said sensing elements coupled to said communication bus whereby information from said sensing elements is disseminated along said communication bus to said sensor readout module.

12. The fiber optic sensing elements of claim 11 whereby at least one of said elements is a hydrogen sensing element.

13. The fiber optic sensing elements of claim 11 whereby at least one of said elements is a temperature sensing element.

14. A process for forming a hydrogen sensing element comprising the steps of:
selecting a porous silica glass member;
doping said member with a solution of photosensitive tungsten hexacarbonyl compound ($WCO_6$) in an alcohol solvent to entrap said compound into said glass member;
exposing said doped member to light to induce a photochemical reaction transforming said hexacarbonyl compound into tungsten oxide ($WO_3$) and permanently binding said tungsten oxide to oxygen atoms in said glass member;
heating said doped member at a temperature to remove said solvent and photoproduced CO gas;
further doping said doped member with a palladium tetrachloride ($PdCl_4$) solution and
heating said further doped member at a temperature to break $PdCl_4$ molecules into palladium metal and chlorine gas and to evaporate chlorine gas products to produce a palladium-tungsten oxide ($Pd/WO_3$) complex in said porous glass member whereby the reaction of said $Pd/WO_3$ complex with hydrogen gas will cause a partial redox reaction of the tungsten oxide and palladium metal to produce a color change in said formed hydrogen sensing element.

15. The process of claim 14 wherein said $Pd/WO_3$ complex comprises equal concentrations of palladium and tungsten oxide.

16. The process of claim 14 wherein said selected porous glass member is produced by a sol-gel process.

17. The process of claim 14 wherein said heating temperature for removing photoproduced CO gas is about 300° C.

18. The process of claim 14 wherein said heating temperature to break said $PdCl_4$ molecules is about 500° C.

19. A multi-point gas sensing network comprising:
a multiplicity of fiber optic sensing elements;
an opto-electronic module containing sensor readout circuitry;
a fiber optic communication bus, said module and said sensing elements coupled to said communication bus whereby information from said sensing elements is disseminated along said communication bus to said sensor readout module; and
said sensor readout circuitry displays the gas concentration and temperature profiles of each element.

20. A multi-point gas sensing network comprising:
a multiplicity of fiber optic sensing elements;
an opto-electronic module containing sensor readout circuitry;
a fiber optic communication bus, said module and said sensing elements coupled to said communication bus whereby information from said sensing elements is disseminated along said communication bus to said sensor readout module; and
said sensor readout circuitry includes an intensity based ratiometric system designed to receive inputs from multiple sensors.

21. A multi-point gas sensing network comprising:
a multiplicity of fiber optic sensing elements;
an opto-electronic module containing sensor readout circuitry;
a fiber optic communication bus, said module and said sensing elements coupled to said communication bus whereby information from said sensing elements is disseminated along said communication bus to said sensor readout module; and
said sensor readout circuitry includes a built-in microprocessor to compensate for fluctuations in temperature and light intensity signals from said elements.

22. A multi-point gas sensing network comprising:
a multiplicity of fiber optic sensing elements;
an opto-electronic module containing sensor readout circuitry;
a fiber optic communication bus, said module and said sensing elements coupled to said communication bus whereby information from said sensing elements is disseminated along said communication bus to said sensor readout module; and
wherein said multiplicity of fiber optic sensing elements includes at least one hydrogen sensor comprising a porous glass body including tungsten oxide and palladium in energy-coupled proximity.

23. A multi-point gas sensing network comprising:
a multiplicity of fiber optic sensing elements;
an opto-electronic module containing sensor readout circuitry;
a fiber optic communication bus, said module and said sensing elements coupled to said communication bus whereby information from said sensing elements is disseminated along said communication bus to said sensor readout module; and
wherein at least one of the sensing elements is a hydrogen sensor and at least one of the sensing elements is a temperature sensor in close proximity to the at least on hydrogen sensor.

24. The network of claim 23 further comprising sensor readout circuitry that compensates for fluctuations in temperature near the at least one hydrogen sensor.

* * * * *